(12) United States Patent
Beeckler et al.

(10) Patent No.: US 10,363,090 B2
(45) Date of Patent: Jul. 30, 2019

(54) CATHETER WITH FLOW DIVERTER AND FORCE SENSOR

(71) Applicant: BIOSENSE WEBSTER (ISRAEL) LTD., Yokneam (IL)

(72) Inventors: Christopher Thomas Beeckler, Brea, CA (US); Assaf Govari, Haifa (IL); Rowan Olund Hettel, Pasadena, CA (US); Tom Allen Ditter, Mission Viejo, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 483 days.

(21) Appl. No.: 14/988,226

(22) Filed: Jan. 5, 2016

(65) Prior Publication Data

US 2017/0189103 A1 Jul. 6, 2017

(51) Int. Cl.
*A61B 5/00* (2006.01)
*A61B 5/06* (2006.01)
(Continued)

(52) U.S. Cl.
CPC .......... *A61B 18/1492* (2013.01); *A61B 5/061* (2013.01); *A61B 5/6852* (2013.01);
(Continued)

(58) Field of Classification Search
CPC .......... A61M 25/0021; A61M 25/0023; A61M 25/0026; A61M 25/0028; A61M 25/0029;
(Continued)

(56) References Cited

U.S. PATENT DOCUMENTS

| 8,357,152 B2 | 1/2013 | Govari et al. |
| 2008/0009750 A1* | 1/2008 | Aeby ............. A61B 5/042 600/478 |

(Continued)

FOREIGN PATENT DOCUMENTS

| CN | 104586499 A | 5/2015 |
| JP | 2014-161452 A | 9/2014 |
| WO | 2015/069887 A1 | 5/2015 |

OTHER PUBLICATIONS

European Search Report dated Jun. 2, 2017 from corresponding European Patent Application No. 17150269.3.

*Primary Examiner* — Michael F Peffley
*Assistant Examiner* — Bradford C. Blaise

(57) ABSTRACT

A catheter probe comprises an insertion tube, and a distal end with a distal electrode, a force sensor to detect force on the distal electrode, and an irrigated electrode mounted on a coupling member of the force sensor, which has a tubular form surrounding a central space occupied by components, including force sensing coils. A fluid diverter that passes fluid to the proximal irrigated electrode is configured as an insert or an integrated projection of the coupling member, which configuration minimizes its space demand within the coupling member. Thus, the diameter of the distal end need not be increased. The fluid diverter has a proximal entry opening and a distal exit opening connected by a fluid passage with at least a radial branch and at least an axial branch. The irrigated electrode is mounted over the distal exit opening to receive fluid from the fluid passage.

16 Claims, 9 Drawing Sheets

(51) Int. Cl.
    *A61B 18/00* (2006.01)
    *A61B 18/14* (2006.01)
    *A61M 25/00* (2006.01)
(52) U.S. Cl.
    CPC .. *A61B 5/6885* (2013.01); *A61B 2018/00029* (2013.01); *A61B 2018/00166* (2013.01); *A61B 2018/00351* (2013.01); *A61B 2018/00577* (2013.01); *A61B 2018/00696* (2013.01); *A61B 2018/00744* (2013.01); *A61B 2018/00755* (2013.01); *A61B 2018/00773* (2013.01); *A61B 2018/00875* (2013.01); *A61B 2218/002* (2013.01); *A61M 25/003* (2013.01); *A61M 25/0029* (2013.01); *A61M 25/0043* (2013.01)
(58) Field of Classification Search
    CPC ............ A61M 25/003; A61M 25/0043; A61M 2025/0034; A61M 2025/0188; A61B 18/1492; A61B 5/061; A61B 5/6852; A61B 5/6885; A61B 2018/00029; A61B 2018/00166; A61B 2018/00577; A61B 2018/00696; A61B 2018/00744; A61B 2018/00755; A61B 2018/00773; A61B 2018/00875; A61B 2218/00; A61B 2218/001; A61B 2218/002; A61B 2560/04; A61B 2562/00; A61B 2562/02
    See application file for complete search history.

(56) References Cited

U.S. PATENT DOCUMENTS

| | | | |
|---|---|---|---|
| 2011/0130648 A1 | 6/2011 | Beeckler et al. | |
| 2013/0253503 A1* | 9/2013 | Govari | A61B 18/1492 606/41 |
| 2014/0336640 A1 | 11/2014 | Beeckler et al. | |
| 2015/0148877 A1* | 5/2015 | Thakkar | A61N 1/05 607/116 |
| 2015/0209105 A1 | 7/2015 | Margallo et al. | |
| 2016/0143690 A1* | 5/2016 | Schultz | A61B 18/1492 606/41 |
| 2016/0374755 A1* | 12/2016 | Mirigian | A61B 18/1492 606/41 |

* cited by examiner

CATHETER WITH FLOW DIVERTER AND FORCE SENSOR

FIELD OF INVENTION

The present invention relates generally to catheters having electrodes, and specifically to catheters wherein the electrodes are irrigated.

BACKGROUND OF INVENTION

Medical procedures involving ablation of the heart may be used to cure a variety of cardiac arrhythmia, as well as to manage atrial fibrillation. Such procedures are known in the art. Other medical procedures using ablation of body tissue, such as treating varicose veins, are also known in the art. The ablation energy for these procedures may be in the form of radio-frequency (RF) energy, which is supplied to the tissue via one or more electrodes of a catheter used for the procedures.

The application of the ablation energy to body tissue, if uncontrolled, may lead to an unwanted increase of temperature of the tissue. It is consequently important to control the temperature of the tissue during any medical procedure involving ablation. One method for control is to irrigate the tissue being ablated. However, irrigation requires components to deliver fluid from a proximal end of the catheter to its distal end. With catheter distal ends having diameters on the order of millimeters, space is often a primary constraint on the design and configuration of distal ends that provide for fluid delivery components. Moreover, with distal ends having tip and ring electrodes, such fluid delivery components must define fluid pathways that can provide axial flow and radial flow but occupy minimal space and avoid interfering with other functional aspects of the distal end, such as force sensing.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

The present invention includes a probe, comprising an insertion tube, a distal electrode, and a proximal electrode. The probe includes a force sensor between the insertion tube and the distal electrode, the force sensor having a coupling member with a proximal portion with a central space and a proximal opening with a slot. The probe further includes a diverter situated in the slot, the diverter having a proximal entry opening and a distal exit opening connected by a fluid passage with a radial branch and an axial branch. A first tubing extends from a proximal end of the insertion tube to the proximal entry opening of the diverter, the first tubing configured to supply irrigation fluid to the fluid passage. Advantageously, the proximal electrode is mounted on the proximal portion of the coupling member, and is positioned over the distal exit opening to receive irrigation fluid delivered by the first tubing.

In some embodiments, the diverter is configured as an insert affixed in the slot.

In some embodiments, the coupling member has a tubular form with a convex outer surface, and the diverter has a corresponding convex outer surface.

In some embodiments, the diverter has an inner surface with a concavity to maximize space and to minimize interference with components occupying or passing through the central space of the coupling member.

In some embodiments, the diverter has an outer surface with an indent formation that extends around a peripheral edge of the outer surface, the indent formation engaging with the slot of the proximal portion of the coupling member.

In some embodiments, the proximal electrode is configured with side wall providing a space gap around the proximal portion, the space gap functioning as a reservoir for irrigation fluid.

In some embodiments, the probe includes an insulating sheath mounted on the proximal portion and the diverter, the sheath having a through-hole aligned with the distal exit opening of the diverter.

In some embodiments, a second tubing extending from a proximal end of the insertion tube to the distal electrode and through the central space of the coupling member, the second tubing configured to supply irrigation fluid to the distal electrode.

In some embodiments, a force sensing coil is housed in the central space without interference by the diverter.

In some embodiments, the diverter is positioned in substantially the same axial plane as the force sensing coil, but at a different azimuthal angle, to avoid interference with one or more force sensing coils housed in the central space.

The present invention is also directed to catheter probe, comprising an insertion tube, a distal electrode, and a proximal electrode. The probe includes a force sensor mounted on a distal end of the insertion tube, the force sensor having a coupling member with a distal portion, a proximal portion, a central space, the distal electrode distal of the coupling member, the proximal electrode mounted on the proximal portion, the force sensor configured to measure a force on the distal electrode, the force sensor having an integrated diverter with a fluid passage connecting a proximal entry opening and a distal exit opening, the diverter configured as a projection extending inwardly into the central space from a side wall of the proximal portion of the coupling member. The probe further includes a first tubing extending from a proximal end of the insertion tube to the proximal entry opening. Advantageously, the proximal electrode is positioned over the distal exit opening to receive irrigation fluid delivered by the first tubing.

In some embodiments, a second tubing extends from a proximal end of the insertion tube to the distal electrode and through the central space of the coupling member, the second tubing configured to supply irrigation fluid to the distal electrode.

In some embodiments, a transmitting coil is housed in the central space of the distal portion, one or more forcing sensing coils being responsive to the transmitting coil.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Overview

An embodiment of the present invention provides a catheter probe which is typically used for a minimally invasive procedure such as ablation of cardiac tissue. The probe comprises an insertion tube, which, in order for it to be minimally invasive, usually has a small outer diameter of approximately 2 mm. At least one electrode, and typically two or more separate electrodes, are mounted on the distal end of the insertion tube (the distal end has approximately the same diameter as the insertion tube).

Mounted within the distal end is a force sensor, which measures the force on the distal end when the end contacts tissue. (Controlling the force enables tissue ablation to be performed more precisely.) The force sensor may have a tubular form that contacts an outer sheath of the insertion tube. The force sensor has a distal central opening, a proximal central opening, and typically defines a central space therebetween.

The one or more electrodes have respective sets of apertures, which are used to supply irrigation fluid to the electrodes and to body material in the region of the electrodes. Irrigation tubing supplies the irrigation fluid to the electrode apertures.

By using the "empty" region within the force sensor, including the proximal central opening and the central space, for the irrigation tubing and component(s), embodiments of the present invention use the available (small diameter) space at the distal end extremely efficiently. This efficient use of the space enables that the electrodes of the distal end to be irrigated during ablation, and also enables force during ablation to be measured, without requiring any increase in diameter of the catheter probe.

System Description

Figure 1:
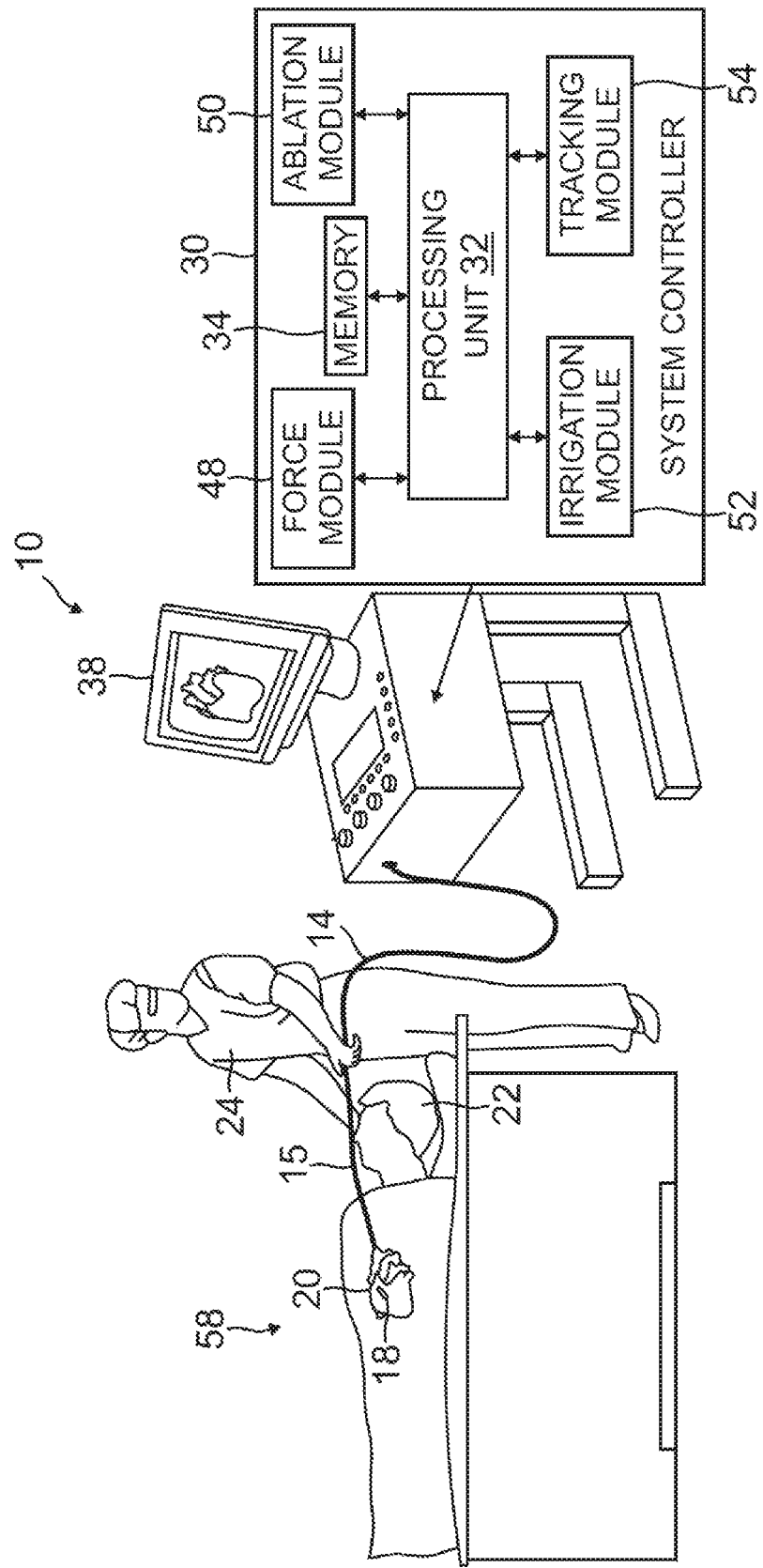
FIG. 1 is a schematic, pictorial illustration of a catheter probe ablating system, according to an embodiment of the present invention.
Figure 2:
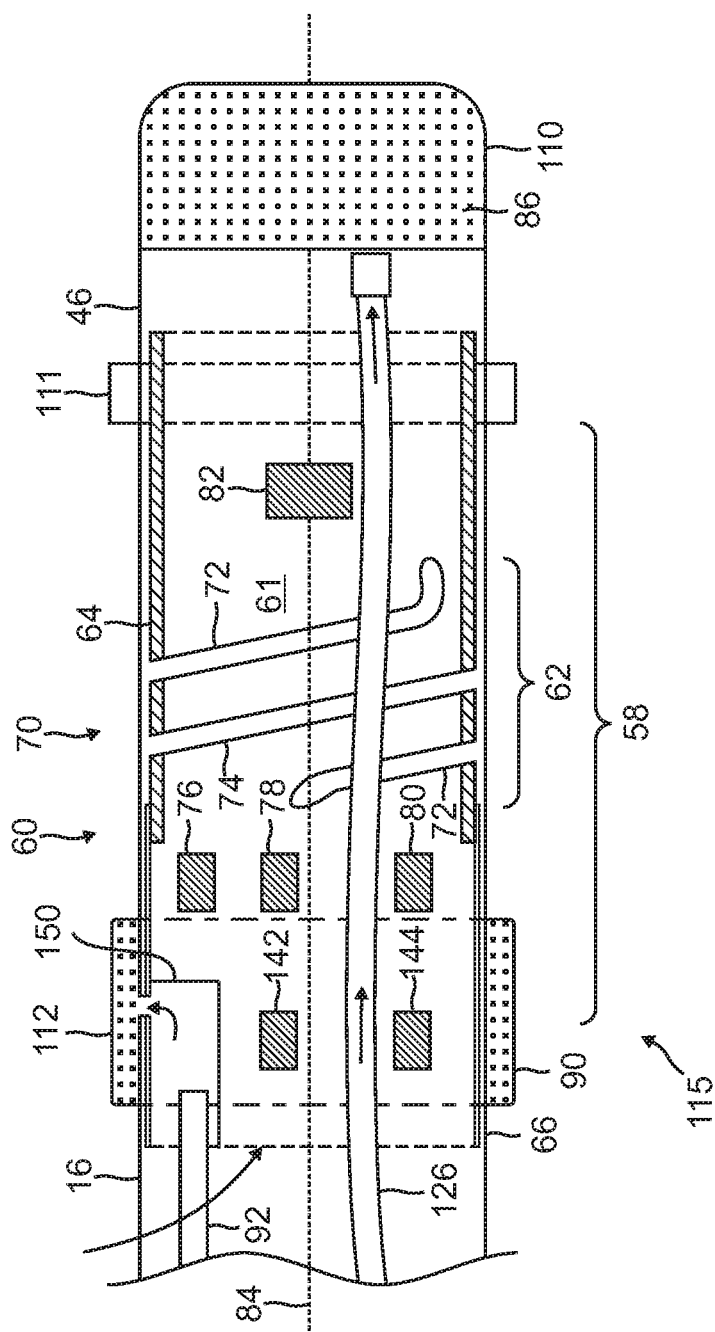
FIG. 2 is a schematic cross-section of a distal end of a catheter probe used in the system having dedicated irrigation tubes, according to an embodiment of the present invention.

Reference is now made to FIG. 1, which is a schematic, pictorial illustration of a catheter probe ablating system 10, and to FIG. 2 which is a schematic cross-section of a distal end of a catheter probe 14 used in the system, according to embodiments of the present invention. In system 10, probe 14 comprises an insertion tube 16, which is inserted into a lumen 18, such as a chamber of a heart 20, of a subject 22. The probe is used by an operator 24 of system 10, during a procedure which typically includes performing ablation of body tissue 26.

For intracardiac operation, insertion tube 16 and distal end 12 should generally have a very small outer diameter, typically of the order of 2-3 mm. Therefore, all of the internal components of catheter probe 14, are also made as small and thin as possible and are arranged so as to, as much as possible, avoid damage due to small mechanical strains.

The functioning of system 10 is managed by a system controller 30, comprising a processing unit 32 communicating with a memory 34, wherein is stored software for operation of system 10. Controller 30 is typically an industry-standard personal computer comprising a general-purpose computer processing unit. However, in some embodiments, at least some of the functions of the controller are performed using custom-designed hardware and software, such as an application specific integrated circuit (ASIC) or a field programmable gate array (FPGA). Controller 30 is typically managed by operator 24 using a pointing device and a graphic user interface (GUI) 38, which enable the operator to set parameters of system 10. GUI 38 typically also displays results of the procedure to the operator.

The software in memory 34 may be downloaded to the controller in electronic form, over a network, for example. Alternatively or additionally, the software may be provided on non-transitory tangible media, such as optical, magnetic, or electronic storage media.

One or more electrodes are mounted on distal end 12. By way of example, FIG. 2 illustrates three such electrodes: a first electrode 110, a second electrode 111, and a third electrode 112, the electrodes being insulated from each other. The electrodes typically comprise thin metal layers formed over an insulating sheath 46 of tube 16. The distal end may have other electrodes, insulated from each other and from electrodes 110, 111, and 112, which for simplicity are not shown in the diagram. Electrode 110, at the extremity of the distal end, by way of example is assumed to have the shape of a cup with a flat base, and is herein also referred to as the cup electrode. Cup electrode 110 typically has a thickness in a range from approximately 0.1 mm to approximately 0.2 mm.

Second electrode 111 is in the form of a ring, and is also referred to herein as ring electrode 111. Ring electrode 111 is typically formed from metal having a similar thickness as the cup electrode. Third electrode 112 is an irrigated ring electrode. In the present disclosure, electrodes 110, 111 and 112, and other electrodes of the distal end, are also referred to herein collectively as electrodes 115.

Electrodes 115 are connected to system controller 30 by conductors in tube 16, not shown in the figures. As described below, at least one of the electrodes is used to ablate tissue 26. In addition to being used for ablation, the electrodes typically perform other functions, as is known in the art; some of the other functions are described below. As necessary, when used for other functions, controller 30 may differentiate between the currents for the different functions by frequency multiplexing. For example, radio-frequency (RF) ablation power may be provided at frequencies of the order of hundreds of kHz, while position sensing frequencies may be at frequencies of the order of 1 kHz. A method of evaluating the position of distal end 12 using impedances measured with respect to the electrodes is disclosed in U.S. Patent Application 2010/0079158 to Bar-Tal et al., which is incorporated herein by reference.

System controller 30 comprises a force module 48, an RF ablation module 50, an irrigation module 52, and a tracking module 54. Processing unit 32 uses the force module to generate and measure signals supplied to, and received from, a force sensor 58 in distal end 12 in order to measure the magnitude and direction of the force on the distal end. The operation and construction of force sensor 58 is described in more detail below.

Processing unit 32 uses the ablation module to monitor and control ablation parameters such as the level of ablation power applied via the one or more electrodes 115. The module also monitors and controls the duration of the ablation that is provided.

Typically, during ablation, heat is generated in the electrode or electrodes providing the ablation, as well as in the surrounding region. In order to dissipate the heat and to improve the efficiency of the ablation process, system 10 supplies irrigation fluid to distal end 12. System 10 uses irrigation module 52 to monitor and control irrigation parameters, such as the rate of flow and the temperature of the irrigation fluid, as is described in more detail below.

Unit 32 uses tracking module 54 to monitor the location and orientation of the distal end relative to patient 22. The monitoring may be implemented by any tracking method known in the art, such as one provided in the Carto3® system produced by Biosense Webster of Diamond Bar, Calif. Such a system uses radio-frequency (RF) magnetic transmitter and receiver elements external to patient 22 and within distal end 12. Alternatively or additionally, the tracking may be implemented by measuring impedances between one or more electrodes, and patch electrodes attached to the skin of patient 22, such as is also provided in the Carto3® system. For simplicity, elements specific to tracking and that are used by module 54, such as the elements and patch electrodes referred to above, are not shown in FIG. 1.

As shown in FIG. 2, distal end 12 is connected to insertion tube 16. The distal end has mounted upon it electrodes 115, and force sensor 58 is mounted within the distal end. Aspects of a force sensor similar to force sensor 58 are described in U.S. Pat. No. 8,357,152, to Govari et al., issued Jan. 22, 2013, and in U.S. Patent Application 2011/0130648, to Beeckler et al., filed Nov. 30, 2009, both of whose disclosures are incorporated herein by reference.

FIG. 2 shows a schematic, sectional view of force sensor 58. Sensor 58 comprises a resilient coupling member 60, which forms a spring joint 62 between two ends of the coupling member. By way of example, coupling member 60 is assumed to be formed in two parts or having two portions, a first part or portion 64 and a second part or portion 66, the two parts being fixedly joined together. The two parts of coupling member 60 are generally tubular, and are joined so that the coupling member also has a tubular form with a central opening. Although there is no necessity that coupling member 60 be formed of two parts, the two-part implementation simplifies assembly of elements comprised in the force sensor, as well as of other elements mounted in the distal end, into the member.

Coupling member 60 typically has one or more helices 70 cut in a portion of the length of first portion 64 of the member, so that the member behaves as a spring. In an embodiment described herein, and illustrated in FIG. 2, helices 70 are formed as two intertwined helices, a first cut helix 72 and a second cut helix 74, which are also referred to herein as a double helix. However, coupling member 60 may have any positive integral number of helices, and those having ordinary skill in the art will be able to adapt the present description without undue experimentation to encompass numbers of helices other than two. Alternatively, the coupling member may comprise a coil spring or any other suitable sort of resilient component with similar flexibility and strength characteristics to those generated by the one or more tubular helical cuts, referred to above.

Coupling member 60 is mounted within and covered by sheath 46, which is typically formed from flexible plastic material. Coupling member 60 typically has an outer diameter that is approximately equal to the inner diameter of sheath 46. Such a configuration, having the outer diameter of the coupling member to be as large as possible, increases the sensitivity of force sensor 58. In addition, and as explained below, the relatively large diameter of the tubular coupling member, and its relatively thin walls, provide a central space 61 enclosed within the coupling member which is occupied by other elements, described below, in the distal end.

When catheter probe 14 is used, for example, in ablating endocardial tissue by delivering RF electrical energy through electrodes 115, considerable heat is generated in the area of distal end 12. For this reason, it is desirable that sheath 46 comprises a heat-resistant plastic material, such as polyurethane, whose shape and elasticity are not substantially affected by exposure to the heat.

Within force sensor 58, typically within the central space 61 of the coupling member 60, a joint sensing assembly, comprising coils 76, 78, 80 and 82, provides accurate reading of any dimensional change in joint 62, including axial displacement and angular deflection of the joint. These coils are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in the sensing assembly are divided between two subassemblies on opposite sides of joint 62: one subassembly comprises coil 82, which is driven by a current, via a cable (not shown) from controller 30 and force module 48, to generate a magnetic field. This field is received by a second subassembly, comprising coils 76, 78 and 80, which are located in a section of the distal end that is spaced axially apart from coil 82. The term "axial," as used in the context of the present patent application and in the claims, refers to the direction of a longitudinal axis of symmetry 84 of distal end 12. An axial plane is a plane perpendicular to this longitudinal axis, and an axial section is a portion of the catheter contained between two axial planes. Coil 82 typically has an axis of symmetry generally parallel to and coincident with axis 84.

Coils 76, 78 and 80 are fixed in distal end 12 at different radial locations. (The term "radial" refers to coordinates relative to the axis 84.) Specifically, in this embodiment, coils 76, 78 and 80 are all located in the same axial plane at different azimuthal angles about the catheter axis, and have respective axes of symmetry generally parallel to axis 84. For example, the three coils may be spaced azimuthally 120° apart at the same radial distance from the axis.

Coils 76, 78 and 80 generate electrical signals in response to the magnetic field transmitted by coil 82. These signals are conveyed by a cable (not shown) to controller 30, which uses force module 48 to process the signals in order to measure the displacement of joint 62 parallel to axis 84, as well as to measure the angular deflection of the joint from the axis. From the measured displacement and deflection, controller 30 is able to evaluate, typically using a previously determined calibration table stored in force module 48, a magnitude and a direction of the force on joint 62.

Controller 30 uses tracking module 54 to measure the location and orientation of distal end 12. The method of measurement may be by any convenient process known in the art. In one embodiment, magnetic fields generated external to patient 22 create electric signals in elements in the distal end, and controller 30 uses the electric signal levels to evaluate the distal end location and orientation. Alternatively, the magnetic fields may be generated in the distal end, and the electrical signals created by the fields may be measured external to patient 22. For simplicity, the elements in distal end 12 that are used to track the distal end are not shown in FIG. 2. However, where such elements comprise coils, at least some of coils 76, 78, 80, and 82 may be used as the tracking elements required in the distal end, in addition to their use as elements of force sensor 58.

At least some of electrodes 115 are configured to have small irrigation apertures. The apertures typically have diameters in an approximate range 0.1-0.2 mm. In the embodiment described herein cup electrode 110 and irrigated ring electrode 112 have respective sets of irrigation apertures 86 and 90. The irrigation fluid for the apertures is supplied by irrigation module 52, which uses tubing 92 to transfer the fluid to the sets of irrigation apertures.

The irrigation fluid is typically normal saline solution, and the rate of flow of the fluid, controlled by module 52, is typically in the range of approximately 10-20 cc/minute, but may be higher or lower than this range.

Tubing 92 delivers fluid to the distal end of the probe. A distal end of the tubing 92 is received in a flow diverter 150 configured in the second (or proximal) portion 66 of the coupling member 60. The fluid is routed to the electrodes by passing through the diverter 150 which is advantageously situated in and through the central space 61 of the coupling member 60 and thus makes no extra demands on the dimensional requirements, particularly the diameter, of the distal end, other than those required for force sensor 58.

In this embodiment, flow diverter 150 may be positioned within or near the axial plane of elliptical coils 142 and 144. For example, flow diverter 150 and elliptical coils 142 and 144 may be spaced radially about catheter axis 84 at different azimuthal angles. This configuration allows flow diverter 150, and therefore, irrigated ring electrode 112 to be positioned relatively distally without interfering with the functionality of force sensor 58. It may be desirable to reduce the distance between cup electrode 110 and ring electrode 112 to provide efficient ablation of the tissue between the electrodes. At the same time, it may also be desirable to position ring electrode 112 proximal to spring joint 122 so as to reduce the distance between cup electrode 110 and force sensor 58, so that force sensor 58 may provide more accurate indication of the position of cup electrode 110.

Figure 3:
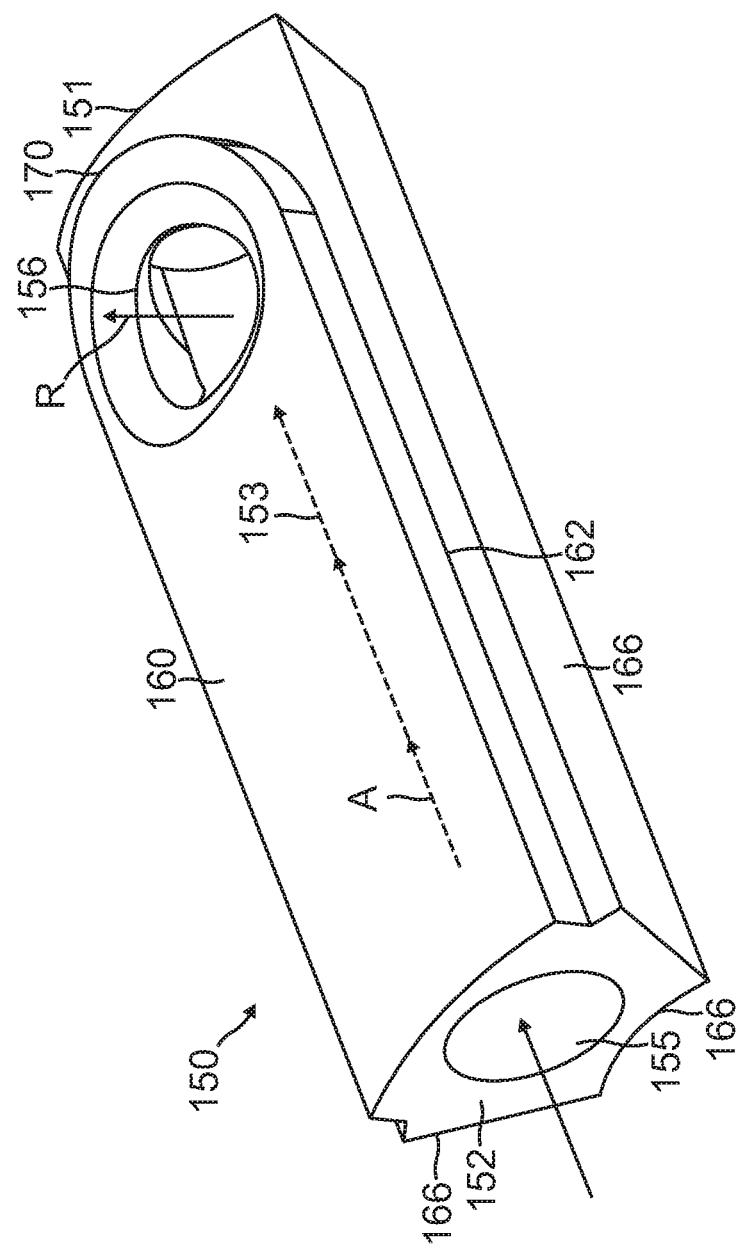
FIG. 3 is a perspective view of a diverter, according to an embodiment of the present invention.
Figure 4:
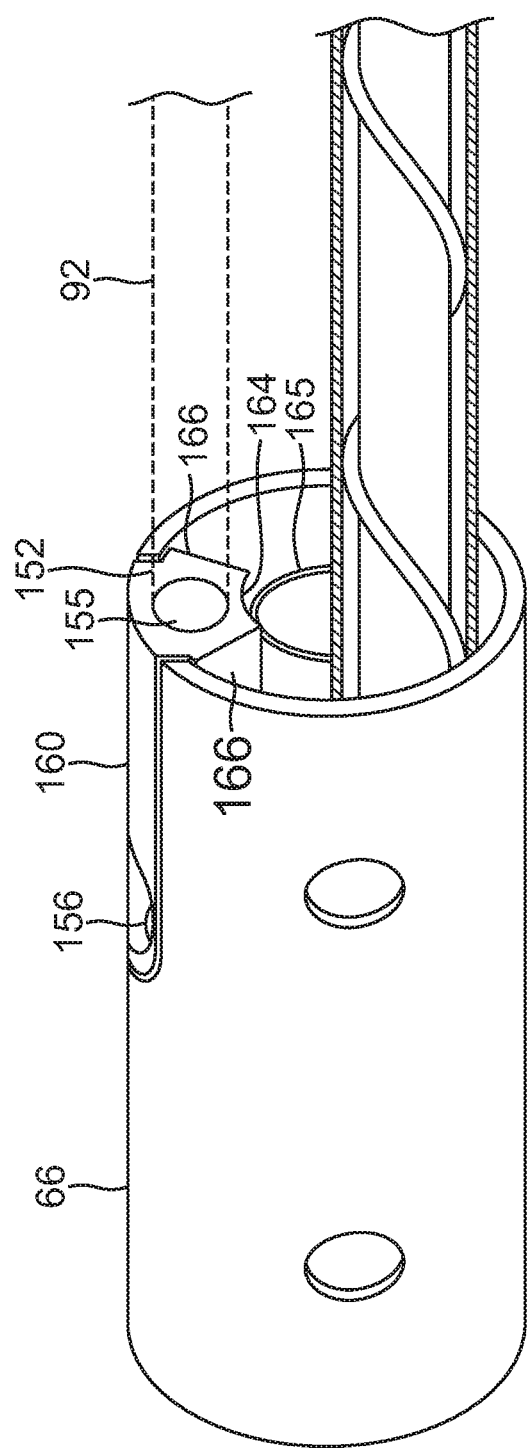
FIG. 4 is a perspective view of a proximal portion of a coupling member with the diverter of FIG. 3, according to an embodiment of the present invention.

In some embodiments, the diverter 150 has an elongated body between a distal end 151 and a proximal end 152, as shown in FIG. 3 and FIG. 4. An outer surface 160 of the diverter body has a convexity with a curvature generally corresponding or matching the outer curvature of the tubular form of the coupling member 60, including the proximal portion 66. On the outer surface 160, a step or indent formation 162 extends around a peripheral edge of the outer surface. The body has tapered radial sides 166 and an inner surface 164 with a concavity.

The diverter body has a fluid passage 153 that connects a proximal entry opening 155, and a distal exit opening 156. The fluid passage 153 includes a proximal axial branch distal of the entry opening 155 and a distal radial branch proximal of the exit opening 155. Thus, fluid entering the diverter through the entry opening 155 is initially guided in an axial direction A, following by a radial direction R before exiting the diverter through the exit opening 156 in the outer surface 160. It is understood that the fluid passage 153 may have any suitable cross-sectional shape, including for example, circular, rectangular, or polygonal.

Figure 5:
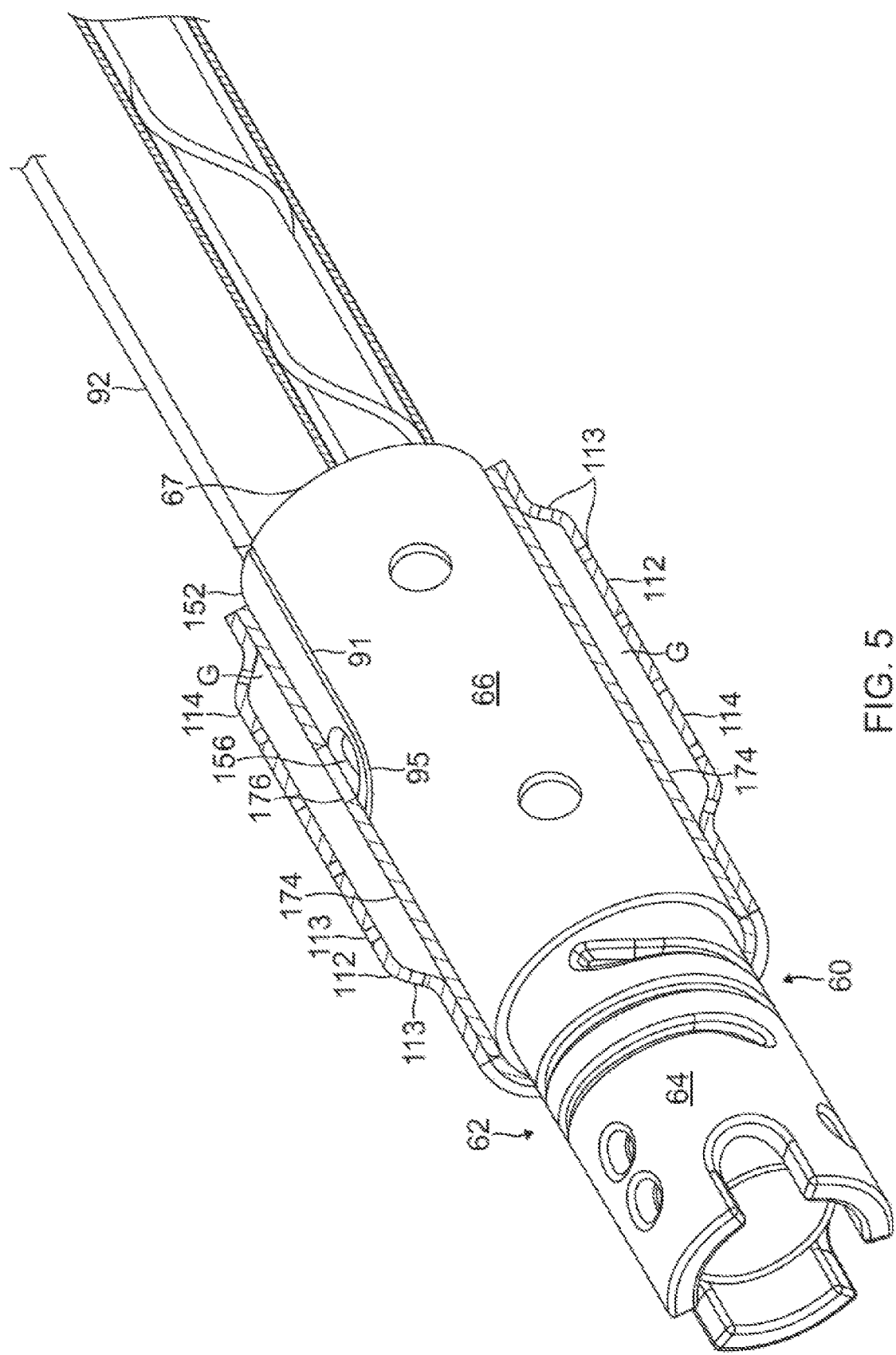
FIG. 5 is a perspective view of a distal end of a catheter probe, with the proximal portion of FIG. 4, according to an embodiment of the present invention.
Figure 6:
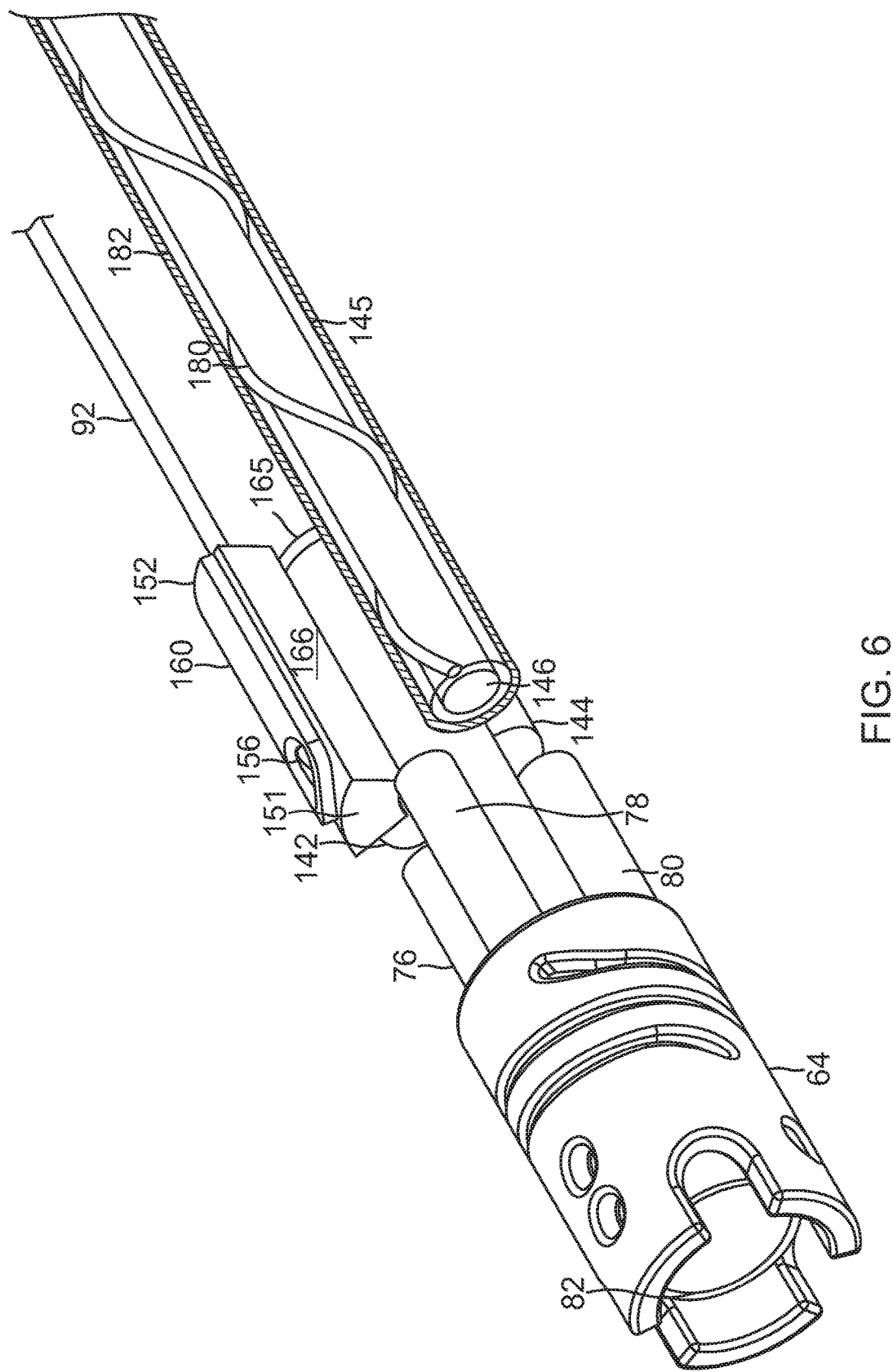
FIG. 6 is the perspective view of the distal end of FIG. 5, with part(s) broken away.

The diverter 150 is positioned in a sidewall 67 of the proximal portion 66 of the coupling member 60. As shown in FIG. 5 and FIG. 6, a proximal end of the proximal portion 66 includes a longitudinal slot 91 defined by an elongated U-shaped edge 95 with a proximal opening that is coextensive with the proximal end 152 of the diverter 150 when inserted in the slot 91. The diverter 150 is inserted into the slot 91 by sliding engagement between the peripheral indent formation 162 and the U-shaped edge 95. The peripheral indent formation 162 has a rounded distal portion 170 that corresponds with the U-shaped edge 95. The outer surface 160 of the diverter 150 is generally flush or even with an outer surface of sidewall of the proximal portion 66. The diverter 150 may be affixed in the slot 91 by adhesive applied between engaged surfaces of the peripheral indent formation 162 and the U-shaped edge 95, which also seals the engaged surfaces. The diverter 150 is constructed of any suitable material, including, for example, PEEK.

As shown in the embodiment of FIG. 3, FIG. 5 and FIG. 6, a distal end of the tubing 92 is inserted and received in the entry opening 155 at the proximal end 152 of the diverter 150. Where the distal end includes a tubular component 165, for example, a guide wire lumen, the inner surface 164 (with its concavity C) of the diverter 150 generally conforms to a convex outer surface of the tubular component 165. The tapered sides 166 minimize the demand on space within the proximal portion 66. For example, the adjacent tapered side does not physically interfere with elliptic coil 142. As shown in FIG. 6, the diverter 150 leaves sufficient room within the central space 61 to accommodate another elliptical coil 144, and at least another tubing 145, for example, with a lumen 146 to pass cables for receiving coils 76, 78 and 80, transmitting coil 82, and/or elliptic coils 142 and 144. Notably, lead wire 180 for cup electrode 112 may be wound on an outer surface of the tubing 145, under a protective nonconductive sheath 182.

As shown in FIG. 5, the ring electrode 112 with apertures 90 is mounted over the proximal portion 66 of the coupling member 60, in particular, over the exit opening 156. The sheath 46 is positioned between the proximal portion 66 and the ring electrode 112 to prevent electrical shorting. The sheath has a through-hole aligned with the exit opening 156.

In use, the diverter 150 receives fluid passed from the tubing 92 into the entry opening 155 which travels through the fluid passage 153 axially and then radially to exit from the exit opening 156 of the diverter 150 and the through-hole 176 of the sheath 46. The fluid then enters a sealed annular space gap G or reservoir provided between the proximal portion 66 (and the sleeve 74), and a sidewall 114 of the ring electrode 112, before exiting the ring electrode 112 via the apertures 90.

Figure 7:
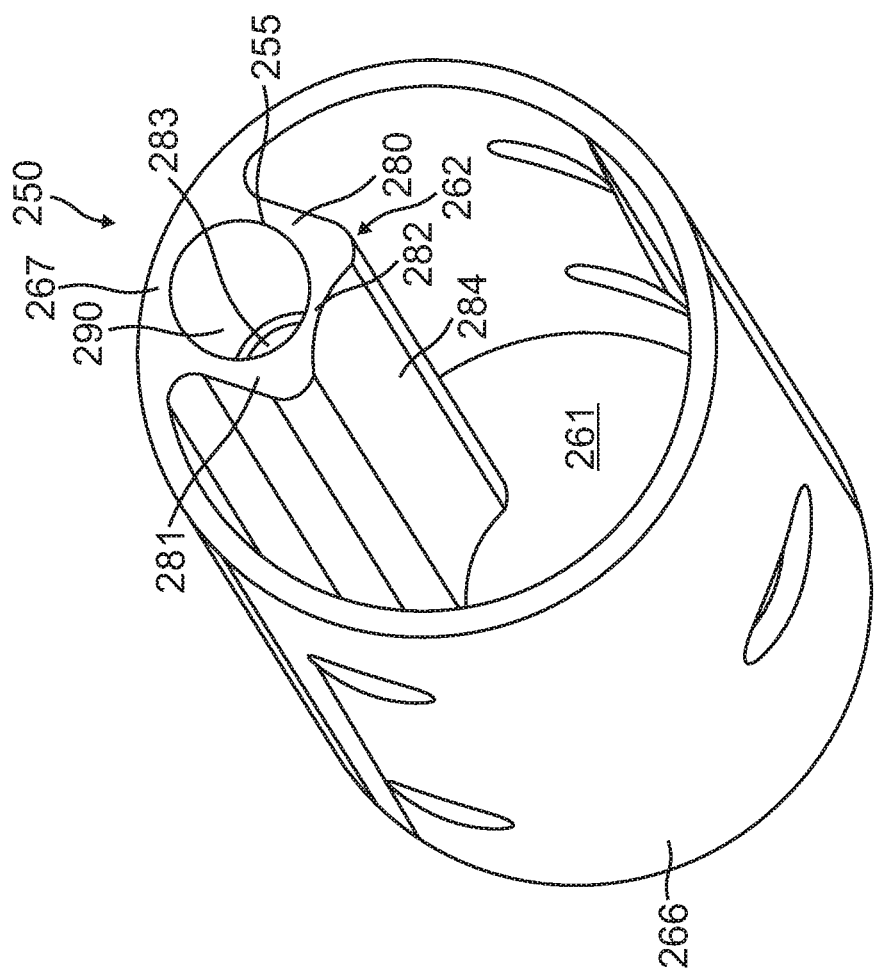
FIG. 7 is a perspective view of a proximal portion of a coupling member with an integrated diverter, according to one embodiment of the present invention.
Figure 8:
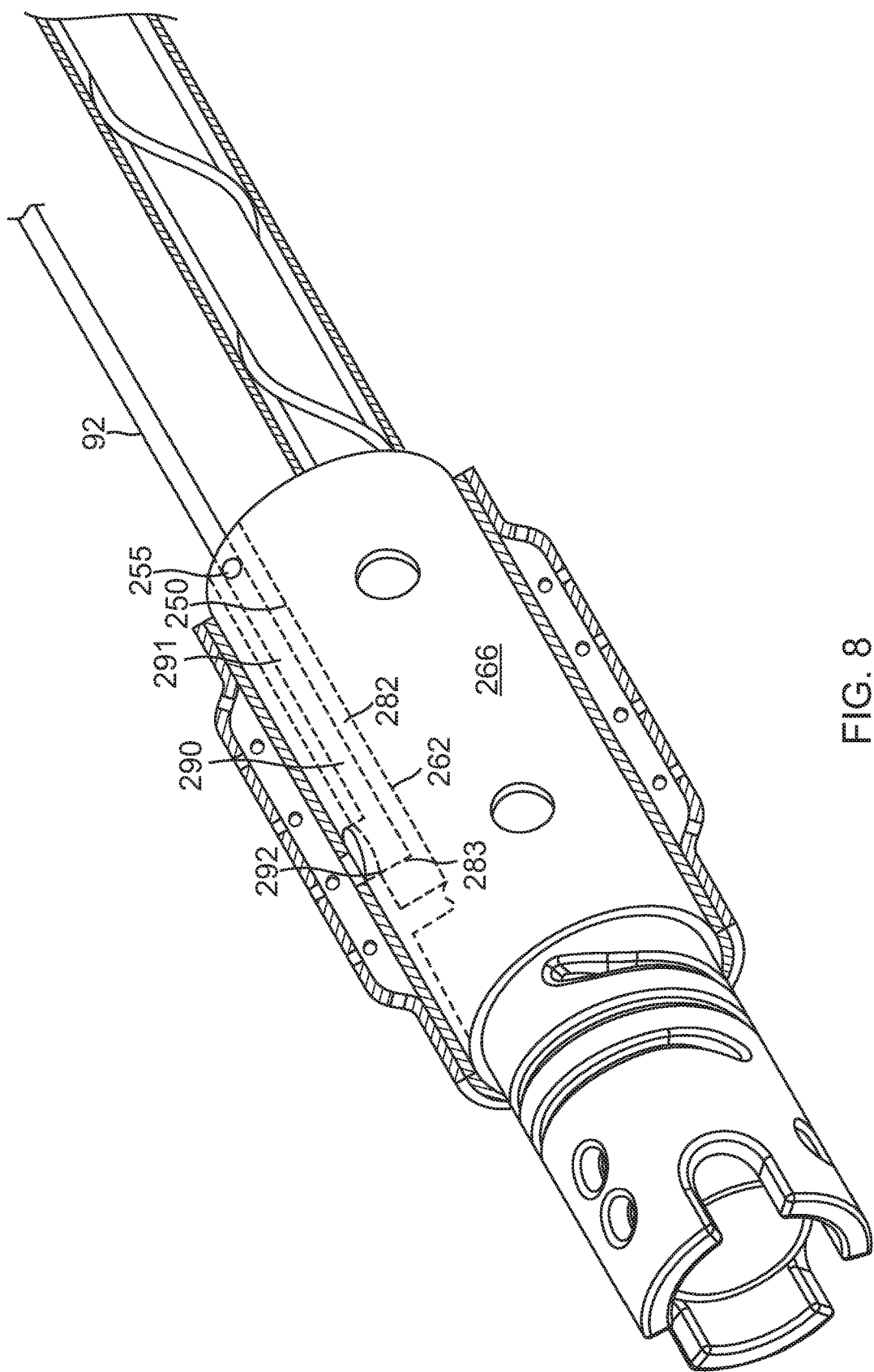
FIG. 8 is a perspective view of a distal end of a catheter probe, with the proximal portion of FIG. 7, according to another embodiment of the present invention.

In other embodiments, a proximal portion 266 of a coupling member has an integrated flow diverter 250, as shown in FIG. 7 and FIG. 8. The diverter 250 is formed in a portion of a radial projection or rib 262 extending inwardly into central space 261 of the proximal portion 266. The radial projection 262 spans longitudinally, along all or a portion of the length of the proximal portion 266. Formed in a proximal portion of the radial projection 262, a fluid passage 290 is defined by sidewalls, including two radial sidewalls 280 and 281, an inner sidewall 282, a distal end sidewall 283 which may be at a predetermined distance from the distal end of the radial projection 262 or a distal end of the proximal portion 266. These sidewalls and a sidewall portion 267 of the proximal portion 266 together define and surround the fluid passage 290, which extends from a proximal entry opening 255 at proximal opening 263 to a distal exit opening 256 proximal to the distal end of the proximal portion 266. The diverter 250 is thus integral with the proximal portion 266. In that regard, the proximal portion 266 and the integrated flow diverter 250 are formed from a single body, of a common material, for example, a superelastic alloy, such as nickel titanium (Nitinol).

The fluid passage 290 includes at least an axial branch 291 and radial branch 292, as shown in FIG. 8. An inner surface 284 of the inner sidewall 282 has a concavity, as shown in FIG. 7, which can conform to a tubular component within the central space 261 of the portion 266

Figure 9:
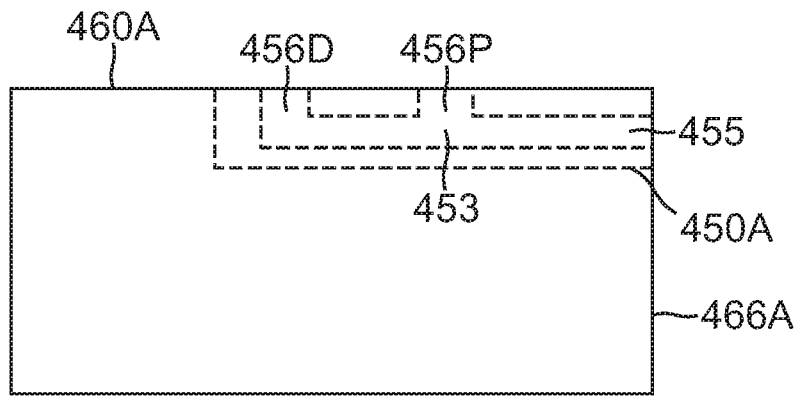
FIG. 9 is a side schematic view of a proximal portion with an integrated diverter, according to another embodiment of the present invention.
Figure 10:
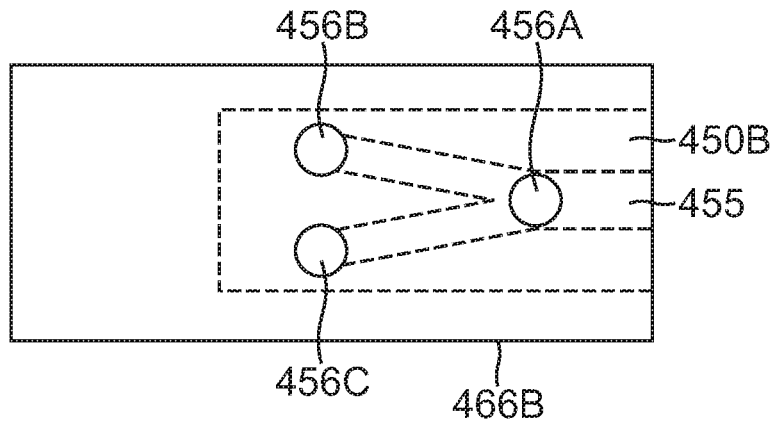
FIG. 10 is a side schematic view of a proximal portion with an integrated diverter, according to another embodiment of the present invention.
Figure 11:
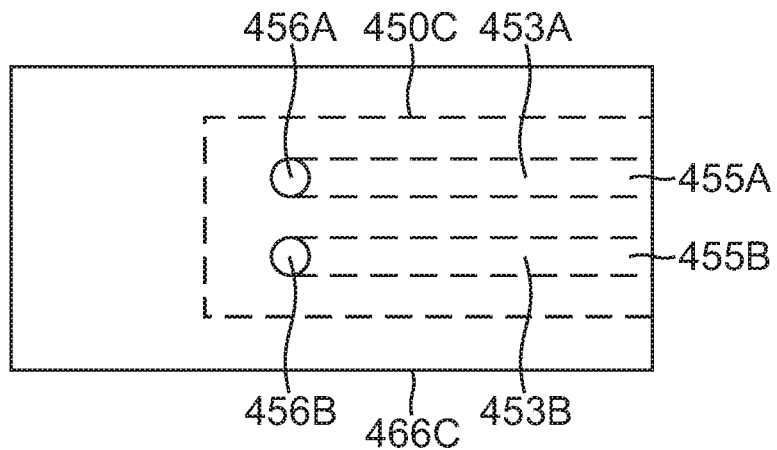
FIG. 11 is a side schematic view of a proximal portion with an integrated diverter, according to another embodiment of the present invention.

It is understood that the fluid passage 290 or 190 may follow any suitable pattern, including combinations of one or more axial or generally axial branches with one or more radial or generally radial branches, between one or more entry openings and one or more exit openings, with dedicated tubing supplying fluid to each entry opening. For example, the fluid passage may include a Y passage having a main axial branch and additional offset branches. In FIG. 9, a diverter 450A of proximal portion 466A has an entry opening 455, a proximal exit opening 456P, a distal exit opening 456D, a fluid passage an axial branch, a proximal radial branch, and a distal radial branch. In FIG. 10, a diverter 450B of proximal portion 466B has a proximal entry opening 455, a proximal exit opening 456A, two distal exit openings 456B and 456C, a fluid passage with an on-axis axial branch and two off-axis axial branch, and three radial branches. In FIG. 11, diverter 450C of proximal portion 466C has two separate and independent entry openings 455A and 455B, each having a fluid passage with a respective axial branch, radial branch and exit opening 456A and 456B.

For any of the foregoing embodiments, controller 30 of FIG. 1 may set the rate of flow to the individual electrodes according to the function performed by the electrode. For example, if an electrode is being used for ablation, controller 30 may increase the flow rate through the electrode compared to when the electrode is not being used for ablation. Alternatively or additionally, controller 30 may alter the flow rate to a particular electrode according to a value of a parameter measured by a sensor in the distal end. Such parameters include the magnitude of the force measured by force sensor 58, as well as the direction of the force measured by the force sensor. Other sensors that the controller may use to alter the flow rate include a temperature sensor in the distal end.

Typically, controller 30 and irrigation module 52 maintain a minimum rate of flow of irrigation fluid to each electrode, to prevent blood entering the irrigation apertures of the electrodes. In some embodiments, rather than having irrigation fluid supplied to the separate electrodes via a common tubing, separate irrigation tubes to each electrode are run from module 52 through probe 14. As shown in FIG. 2, distal cup electrode 110 is fed by dedicated irrigation tube 126.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention, and that the drawings are not necessarily to scale. Moreover, it is understood that any one feature of an embodiment may be used in lieu of or in addition to feature(s) of other embodiments. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A probe, comprising:
    an insertion tube;
    a distal electrode;
    a proximal electrode;
    a force sensor between the insertion tube and the distal electrode, the force sensor having a coupling member with a proximal portion with a central space and a proximal opening with a longitudinal-slot having a u-shaped edge, the force sensor configured to measure a force on the distal electrode;
    a diverter having an outer surface with a curvature generally corresponding to an outer curvature of the coupling member, the diverter having an indent formation extending around a peripheral edge of the outer surface of the diverter with the peripheral edge of the diverter having a rounded distal portion such that the diverter is positioned in the longitudinal slot with the rounded distal portion of the diverter corresponding with the u-shaped edge of the slot, the diverter having a proximal entry opening and a distal exit opening, the diverter having a fluid passage with a radial branch and an axial branch; and
    a first tubing extending from a proximal end of the insertion tube to the proximal entry opening of the diverter, the first tubing configured to supply irrigation fluid to the fluid passage,
    wherein the proximal electrode is mounted on the proximal portion of the force sensor, and is positioned over the distal exit opening.

2. The probe of claim 1, wherein the diverter is configured as an insert affixed in the slot.

3. The probe of claim 1, wherein the diverter has an inner surface with a concavity.

4. The probe of claim 1, wherein the proximal electrode is configured with a side wall providing a space gap around the proximal portion.

5. The probe of claim 1, further comprising an insulating sheath mounted on the proximal portion and the diverter, the sheath having a through-hole aligned with the distal exit opening of the diverter.

6. The probe of claim 1, further comprising a second tubing extending from the proximal end of the insertion tube to the distal electrode, the second tubing configured to supply irrigation fluid to the distal electrode.

7. The probe of claim 1, further comprising a force sensing coil housed in the central space.

8. The probe of claim 7, wherein the diverter is positioned in substantially the same axial plane as the force sensing coil, but at a different azimuthal angle.

9. A catheter probe, comprising:
    an insertion tube;

a distal electrode;

a proximal electrode;

a force sensor mounted on a distal end of the insertion tube, the force sensor having a coupling member with a distal portion, a proximal portion and a proximal opening with a longitudinal slot having an u-shaped edge, a central space, the distal electrode mounted on the distal portion, the proximal electrode mounted on the proximal portion, the force sensor configured to measure a force on the distal electrode, the force sensor having a diverter with a fluid passage between a proximal entry opening and a distal exit opening, the diverter having an outer surface with a curvature generally corresponding to an outer curvature of the coupling member, the diverter having an indent formation extending around a peripheral edge of the outer surface of the diverter with the peripheral edge of the diverter having a rounded distal portion such that the diverter is positioned in the longitudinal slot with the rounded distal portion of the diverter corresponding with the u-shaped edge of the slot, the diverter configured as a radial projection extending inwardly from a side wall of the proximal portion into the central space; and a first tubing running from a proximal end of the insertion tube to the proximal entry opening of the fluid passage, wherein the proximal electrode is positioned over the distal exit opening.

10. The probe of claim 9, wherein the diverter has an inner surface with a concavity.

11. The probe of claim 9, wherein the proximal electrode is configured with a side wall providing a space gap around the proximal portion.

12. The probe of claim 9, further comprising an insulating sheath mounted on the proximal portion and the diverter, the sheath having a through-hole aligned with the distal exit opening of the diverter.

13. The probe of claim 9, further comprising a second tubing extending from the proximal end of the insertion tube to the distal electrode, the second tubing configured to supply irrigation fluid to the distal electrode.

14. The probe of claim 9, further comprising a force sensing coil housed in the central space of the proximal portion.

15. The probe of claim 14, wherein the diverter is positioned in substantially the same axial plane as the force sensing coil, but at a different azimuthal angle.

16. The probe of claim 14, further comprising a transmitting coil housed in the central space of the distal portion.

* * * * *